(12) United States Patent
Carr

(10) Patent No.: US 8,440,949 B2
(45) Date of Patent: May 14, 2013

(54) IN-LINE MICROWAVE WARMING APPARATUS

(75) Inventor: Kenneth L. Carr, Woolwich, ME (US)

(73) Assignee: Meridian Medical Sysstems, LLC, Woolwich, NE (US)

(*) Notice: Subject to any disclaimer, the term of this patent is extended or adjusted under 35 U.S.C. 154(b) by 1382 days.

(21) Appl. No.: 12/115,075

(22) Filed: May 5, 2008

(65) Prior Publication Data

US 2008/0277389 A1    Nov. 13, 2008

Related U.S. Application Data

(63) Continuation-in-part of application No. 11/745,507, filed on May 8, 2007, now Pat. No. 7,989,741.

(51) Int. Cl.
*H05B 6/72* (2006.01)

(52) U.S. Cl.
USPC .................. 219/761; 219/693; 607/101

(58) Field of Classification Search .......... 219/628–630, 219/678, 679, 687–696, 702, 704, 710–713, 219/762, 761; 604/27, 48, 114; 607/90, 98–106; 606/27–31; 422/1, 21, 186; 600/549; 128/898
See application file for complete search history.

(56) References Cited

U.S. PATENT DOCUMENTS

| | | | | |
|---|---|---|---|---|
| 3,806,837 A | * | 4/1974 | Carr et al. | 333/1.1 |
| 4,122,324 A | * | 10/1978 | Falk | 219/729 |
| 5,073,167 A | | 12/1991 | Carr et al. | |
| 5,683,381 A | * | 11/1997 | Carr et al. | 606/27 |
| 5,782,897 A | | 7/1998 | Carr | |
| 5,919,218 A | * | 7/1999 | Carr | 607/100 |
| 6,843,673 B1 | * | 1/2005 | Liu et al. | 439/188 |
| 7,128,275 B2 | * | 10/2006 | Kammer et al. | 236/1 C |
| 2008/0310995 A1 | * | 12/2008 | Charm et al. | 422/21 |

* cited by examiner

*Primary Examiner* — Tu B Hoang
*Assistant Examiner* — Thien S Tran
(74) *Attorney, Agent, or Firm* — Cesari and McKenna, LLP

(57) ABSTRACT

Microwave warming apparatus includes a housing defining a heating waveguide with a longitudinal ridge and a heating cavity. A slot extends through the ridge into the heating cavity for receiving a cartridge containing a looped tube so that the tube extends into the heating cavity where the tube contents are heated by energy coupled into the waveguide. Receiving waveguides adjacent to the slot sense the thermal radiation emanating from the tube and deliver corresponding signals to a radiometer which produces a temperature indication. The cartridge includes a support member which maintains the shape of the tube loop. A pair of notches in the support member have walls enabling the notches to complete the receiving waveguides in the housing.

30 Claims, 7 Drawing Sheets

IN-LINE MICROWAVE WARMING APPARATUS

RELATED APPLICATION

This application is a continuation-in-part of Ser. No. 11/745,507, filed May 8, 2007, now U.S. Pat. No. 7,989,741.

BACKGROUND OF THE INVENTION

1. Field of the Invention

This invention relates to in-line microwave warming apparatus for warming blood and other fluids. It relates especially to a cartridge for use in such apparatus.

2. Background Information

In many applications, particularly in the medical field, there may be a requirement that a circulating fluid be warmed. For example, in cardiac surgery during extra-corporeal circulation (ECC), the patient is first cooled in order to slow metabolism and thereafter the circulating blood is warmed to return it to body temperature. As other examples, heated intravenous fluids are useful in hypothermic patients and in trauma patients requiring massive IV resuscitation and heated fluids are useful for wound irrigation.

Microwave energy has, in the past, been used in connection with the heating of blood and intravenous fluids. For example, my U.S. Pat. Nos. 5,073,167 and 5,919,218, whose entire contents are incorporated herein by reference, disclose microwave apparatus comprising a waveguide heating cavity having a source of microwave energy coupled thereto. A support element encircled by a fixed length of tubing forms a disposable cartridge which may be positioned in the heating cavity. The characteristics, and placement within the heating cavity, of the cartridge are such that there results a rapid, uniform heating of the fluid flowing through the cartridge.

Such prior apparatus also includes means for non-invasively monitoring the temperature of fluid flowing through the cartridge and thereby controlling the energy source so as to maintain the flowing fluid at a selected temperature. These means include an external fluid inlet temperature transducer and an external fluid outlet temperature transducer. Since these transducers are external to the heating cavity, a third transducer is needed to measure the temperature of the fluid within the cavity. This is necessary to address the situation wherein the fluid flow is suddenly stopped for some reason and the output transducer is calling for heat because it senses a temperature drop. In other words, the fluid could severely overheat before the outlet transducer recognizes the problem. Resultantly, when flow resumes, the overheated fluid could injure the patient.

While the above-described patented in-line microwave warmers provide distinct advantages over the prior water immersion-type warmers, they have certain drawbacks which may limit their use and application. For example, as noted above, they require three separate temperature monitors each of which consists of a transducer and a radiometer. Also, the cartridges in the patented apparatus require multiple turns of tubing in order to achieve the desired warming effect. Such a multi-turn tubing cartridge is quite large and has a relatively large priming volume, in the order or 4 ml. In addition, the large cartridge necessitates a commensurately large opening in the heating cavity in order to receive the cartridge. This means that steps must be taken to ensure that microwave radiation does not leak from the heating cavity at that opening. For example, the patented cartridge is provided with a complex metal ground plane to inhibit such radiation leakage.

Still further, in the prior apparatus reflected in the above patents, the transducer in the heating cavity receives signals from all of the windings in the cartridge and accordingly senses the average temperature of the fluid in the multiple windings rather than the temperature of the fluid just as the fluid exits the heating cavity.

Still further, the two external transducers, three separate external radiometers and the multiple cables connecting the various temperature transducers to the radiometers, increase the overall complexity and footprint of the prior apparatus.

SUMMARY OF THE INVENTION

Accordingly, it is an object of the present invention to provide in-line microwave warming apparatus having dramatically reduced complexity and parts count which, in turn, minimizes the cost of the apparatus.

Another object of the invention is to provide in-line microwave warming apparatus whose cartridge is small enough to be received in a thin opening into the heating cavity so that minimal radiation can enter or leave the cavity via that opening.

Yet another object of the invention is to provide apparatus of this type whose cartridge consists of a single tubing turn having a minimal priming volume.

A further object of the invention is to provide in-line microwave warming apparatus which requires only two temperature monitors both of which are inside the apparatus so that external transducers, radiometers and cables thereto are not required.

Another object of the invention is to provide in-line microwave warming apparatus of this type whose cartridge includes parts of the aforesaid temperature monitors.

Yet another object is to provide an improved in-line cartridge for microwave warming apparatus of this general type.

Still another object is to provide such a cartridge which is of a simple construction yet which helps to minimize radiation leakage from the apparatus.

Other objects will, in part, be obvious and will, in part, appear hereinafter. The invention according comprises the features of construction, a combination of elements and arrangement of parts which will be exemplified in the following detailed description, and the scope of the invention will be indicated in the claims.

Briefly, my apparatus comprises a three-dimensional waveguide which defines a heating cavity. Microwave energy from a microwave transmitter is coupled to the waveguide at a location spaced longitudinally from the heating cavity as described in my above patents. An opening in a form of a thin slot is provided in one of the walls of the waveguide at the heating cavity to accommodate an in-line cartridge.

In this case, however, the cartridge comprises a single turn or loop of tubing whose opposite ends are terminated by connectors. The tubing turn is supported and shaped by a flat, dielectric support member so that the tubing turn has opposite legs which are straight, coplanar and spaced apart a selected distance as will be described later. The cartridge is arranged to be slid into the slot in the waveguide so that the tube legs extend more or less perpendicular to the longitudinal axis of the waveguide at the heating cavity. When the cartridge is so seated in the heating cavity, the slot and cartridge are sufficiently thin or narrow as to prevent leakage of radiation to or from the heating cavity.

An internal longitudinal conductive ridge projects from the waveguide wall containing the slot. This ridge is aligned with the slot and may extend the entire length of the waveguide. Thus, the slot passes through the ridge into the heating cavity.

Also, portions of the housing comprise, with the cartridge support member, a pair of receiving waveguides that form internal transducers for detecting thermal radiation from fluid in the cartridge tube just as the fluid enters and leaves the heating cavity.

More particularly, the cartridge support member includes a pair of notches in its opposite sides which are spaced a selected distance from the lower end of that member. As we shall see, these notches complete the abovesaid receiving waveguides in the housing. Also, a tube is engaged to those sides, the tube having a bridging segment extending under the lower end of the support member, an inlet and an outlet located above the upper end of the support member and segments bridging the pair of notches. Preferably, the walls of those notches are electrically conductive so that they can function as backplates for the aforesaid receiving waveguides.

The waveguide-detected signals are led out of the heating cavity via waveguide-to-MIC conductor transitions which are part of a printed circuit present inside the apparatus. That circuit includes a radiometer and a switch which connects the transitions alternatively to the radiometer so that the same radiometer can provide both fluid inlet and outlet temperature signals. These signals are then used to control a display. The radiometer signals may also be employed to control the heating transmitter to change the warming characteristics of the apparatus.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN
ILLUSTRATIVE EMBODIMENT

Figure 1:
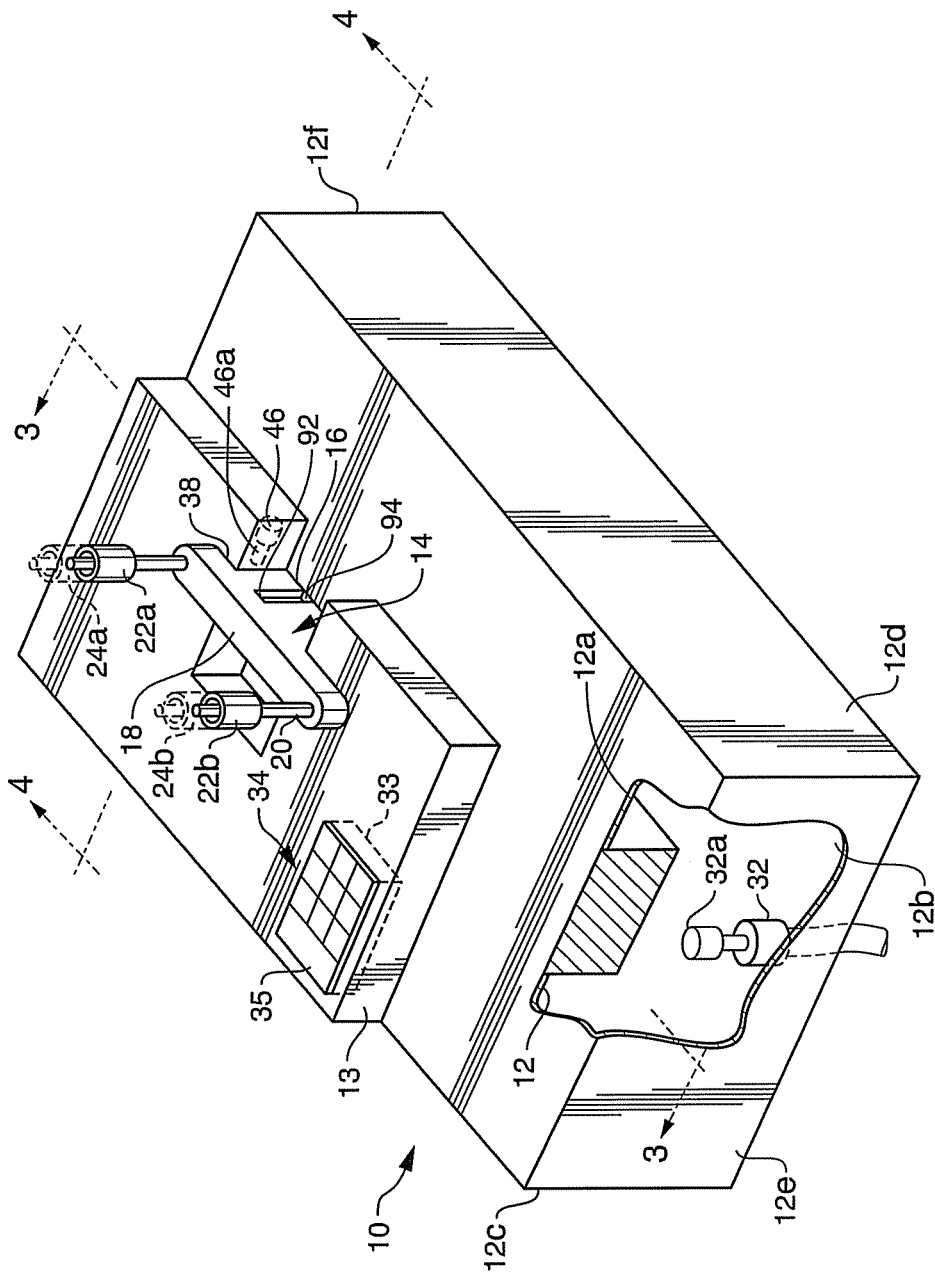
FIG. 1 is an isometric view, with parts cut away, showing in-line microwave warming apparatus incorporating the invention.

Referring to FIG. 1 of the drawings, my apparatus comprises a housing shown generally at 10 which defines a longitudinally extending waveguide 12 with a C-shaped promontory 13 atop the waveguide. The apparatus also includes a cartridge indicated generally at 14 which may be received in a slot 16 in housing 10 so that the cartridge protrudes through the arms of promontory 13 into the waveguide 12. If desired, housing 10 may include a conventional door mechanism (not shown) to hold the cartridge in the slot 16.

Cartridge 14 comprises a support member 18 which supports a length of tubing 20 whose opposite ends are terminated by conventional connectors 22a and 22b. Connector 22a, usually a female connector, may be connected to a mating connector 24a at the end of tubing leading to a source of fluid such as a blood bag or fluid administration set (not shown). Connector 22b, usually a male connector, may be connected to a mating connector 24b at the end of tubing leading to a fluid destination such as a catheter (not shown). As is evident from FIG. 1, the waveguide 12 has a pair of relatively broad upper and lower walls 12a and 12b, respectively, a pair of narrower side walls 12c and 12d, respectively, and a pair of end walls 12e and 12f, respectively. The waveguide is thus a three-dimensional body having a width (X direction), a height (Y direction) and a length (Z direction) which defines a heating cavity 12' (FIGS. 3 and 4) within the waveguide. The slot 16 opens into cavity 12' and the cartridge 14, including its tube 20, projects through the slot into that cavity.

At the heating cavity 12' of the waveguide, fluid flowing through tube 20 is heated by energy from a microwave transmitter (not shown) coupled into the waveguide 12 by means of a coaxial-to-waveguide connector 32 mounted in the bottom wall 12b of housing 10 at a location spaced along the waveguide 12, i.e. in the Z direction, from the heating cavity 12'.

The connector 32, which may be a standard type N connector, has a probe 32' which projects into waveguide 12 and functions as an antenna to conduct electromagnetic energy (TEM) from the connector into the waveguide so that the energy propagates in a $TE_{10}$ mode for the particular dimensions of the waveguide. While these dimensions may vary, the illustrated waveguide 12 may be 3.40 inches wide and 1.65 inches high. For a microwave transmitter operating at a frequency of 2.45 GHz, these dimensions place the frequency of operation in an ideal location in the frequency spectrum. That is, the frequency is sufficiently far enough from the cut-off frequency (1.37 GHz) so that minimum attenuation is obtained for the $TE_{10}$ mode of propagation and yet higher order modes are cut-off.

Of course, instead of a coaxial-to-waveguide transition between the microwave transmitter and the apparatus 10, a suitable feed waveguide (not shown) may extend from the transmitter to housing 10.

In order to couple the maximum amount of energy into the waveguide 12, the connector 32 (or feed waveguide) should be positioned from the adjacent end wall 12e of waveguide 12 a distance equal to one quarter wavelength or multiple thereof at the transmitter frequency, as described in the above patents. The microwave energy coupled to the heating cavity 12' of waveguide 12 warms the fluid flowing through cartridge 14 quite efficiently.

In a manner described in the above patents, the illustrated apparatus monitors the temperature of the fluid flowing through cartridge 14 at the heating cavity 12' and uses that information to regulate the microwave energy coupled into the waveguide 12. In this way, the temperature of the fluid leaving cartridge 14 may be maintained at a selected value independently of the fluid flow rate and the fluid inlet temperature.

The operation of apparatus 10 is controlled by a controller 33 mounted in the apparatus, e.g. in promontory 13. Control settings, e.g. desired temperature, warming time, etc., may be set into the controller 33 via a keypad 34 exposed in the housing at the upper surface of the promontory and relevant data maybe displayed by an LCD display 35 positioned next to the keypad and controlled by controller 33.

Figure 2:
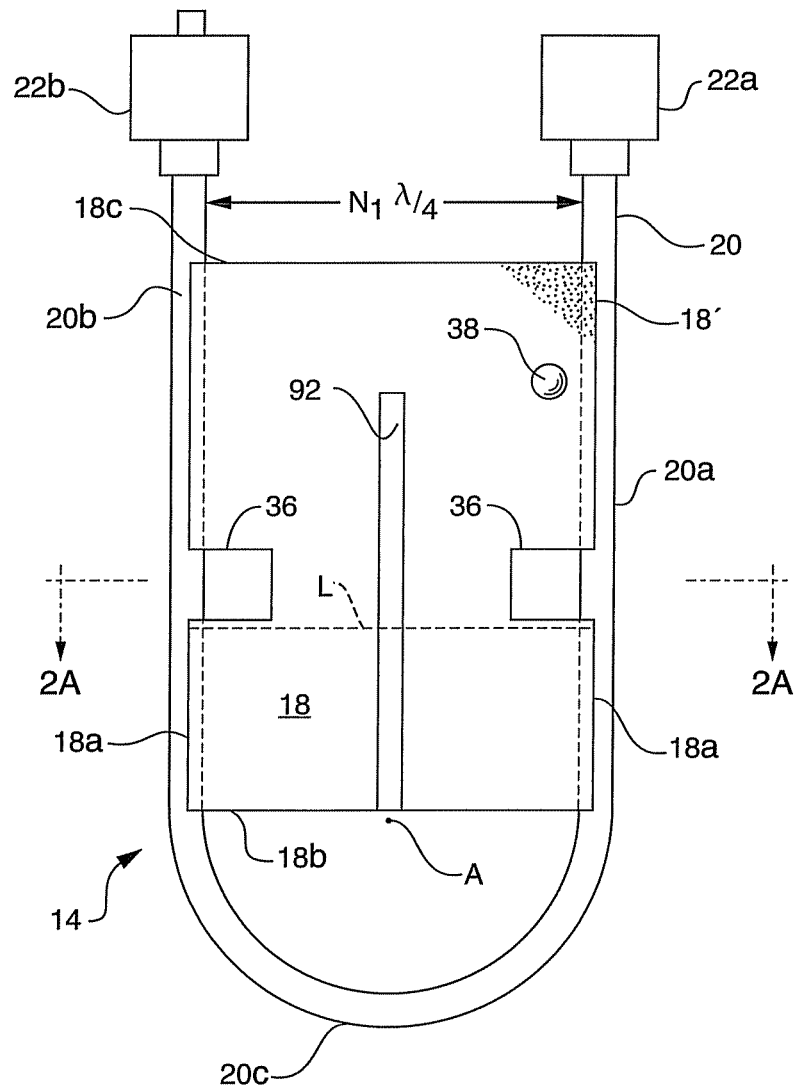
FIG. 2 is a front elevational view of the cartridge component of the FIG. 1 apparatus.
Figure 2A:
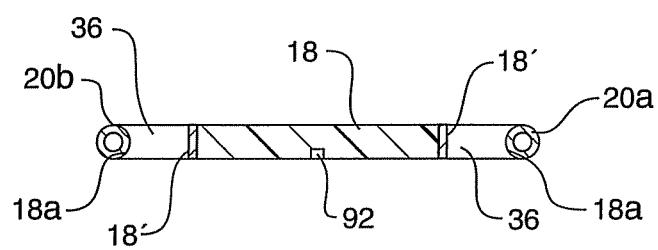
FIG. 2A is a sectional view taken along line 2A-2A of FIG. 2.

Refer now to FIGS. 2 and 2A which show the cartridge 14 in greater detail. It is preferably a disposable item comprising a single turn or loop of the plastic tubing 20 which is wrapped around and supported by support member 18. Preferably, tube 20 is relatively short, e.g. 9.0 inches and has a relatively small internal diameter, e.g. 0.131 inch, so that cavity 14 has a small flow priming volume, i.e. less than 1.0 ml, yet still allows unrestricted fluid flow through the apparatus. Member 18 consists of a flat plate whose opposite side walls 18a, 18a are straight, parallel and concave to bed the two legs or segments 20a and 20b of tube 20 so that those legs are straight, parallel and coplanar. The tube segments 20a, 20b may be secured to support member 18 by a suitable adhesive or by RF welding. The bridging segment 20c of tube 20 that extends between the tube legs 20a, and 20b is more or less a semi-circle having an axis A located at or adjacent to the lower end 18b of support member 18.

Figure 5:
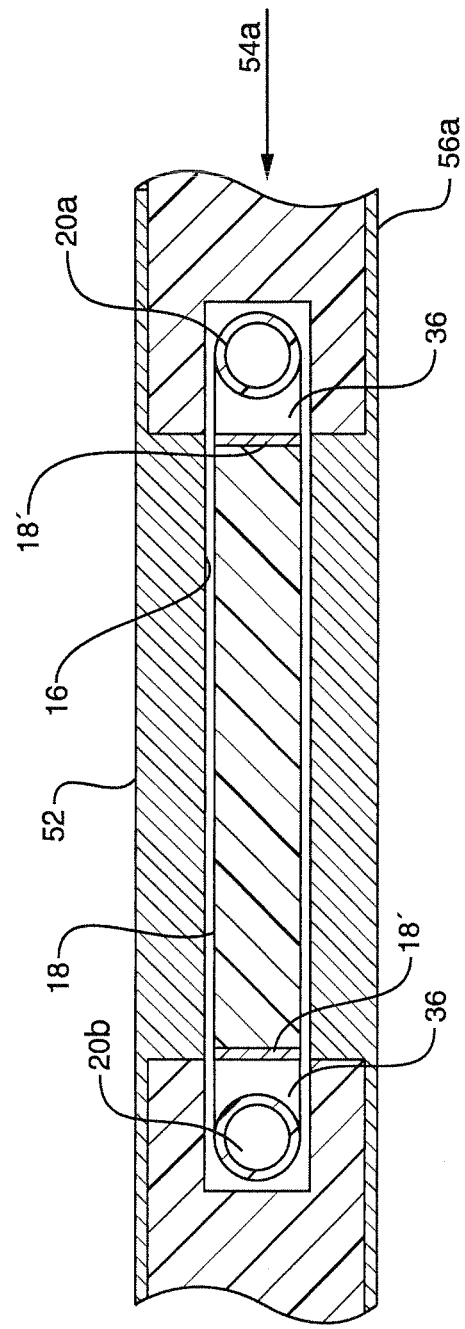
FIG. 5 is a fragmentary sectional view on a larger scale taken along line 5-5 of FIG. 4.

For reasons that will be described later, the support member 18 has a pair of opposed notches 36 extending in from the side edges 18a, 18a of the support member. These notches are positioned so that when cartridge 14 is inserted into housing 10, they coact with the structure therein to help form a pair of transducers $T_I$ and $T_O$ (FIG. 3) that sense the temperature of the fluid flowing into and out of the cartridge 14. The support member 18 is molded of a lightweight, relatively rigid dielectric material such as polystyrene and has metallized surfaces 18' at the walls of notches 36 as best seen in FIGS. 2, 2A and 5 so that those walls are electrically conductive. The upper edge margin of member 18, i.e. above line L in FIG. 2, may also have a conductive metal coating 18' all around for reasons that will be described later. Suffice it to say here that this is the margin of support 18 that lies above cavity 12' when cartridge 14 is seated in housing 10.

Preferably, the width of the support member 18 should be such that the spacing of the two tube legs 20a, 20b is substantially equal to a quarter wavelength or multiple thereof at the operating frequency of the transmitter, i.e. $N_1 \lambda_T/4$. This spacing, which is about 1.8 inches for the illustrated cartridge 14, provides a matched load at the aforesaid heating frequency. Preferably also, the support member 18 should be formed with a dimple or detent 38 near an upper corner thereof. As will be described later, the dimple helps to releasably retain cartridge 14 at its seated position in slot 16 of housing 10 and contributes to an interlock.

Figure 3:
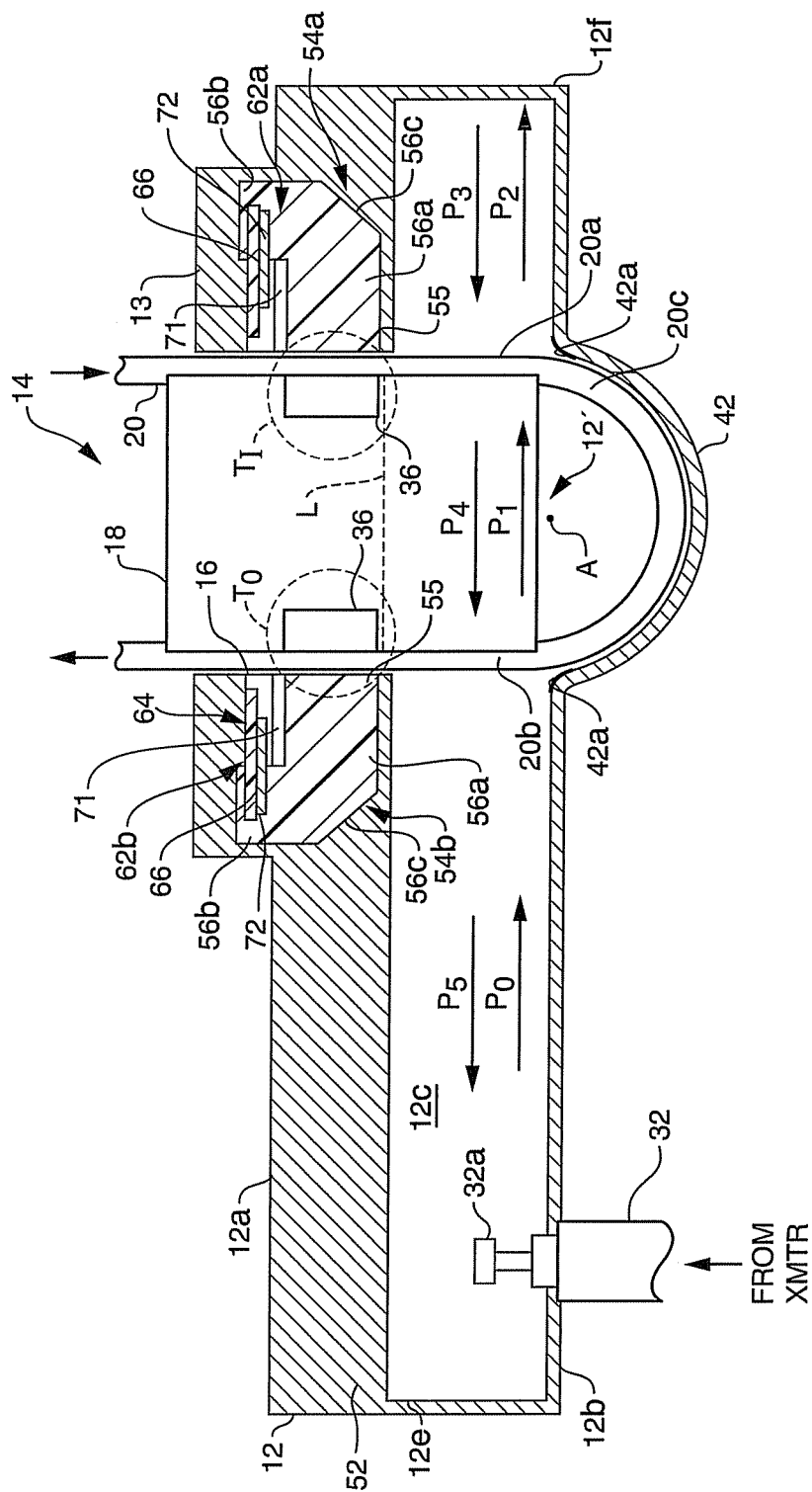
FIG. 3 is a sectional view, with parts shown in elevation, taken along line 3-3 of FIG. 1.
Figure 4:
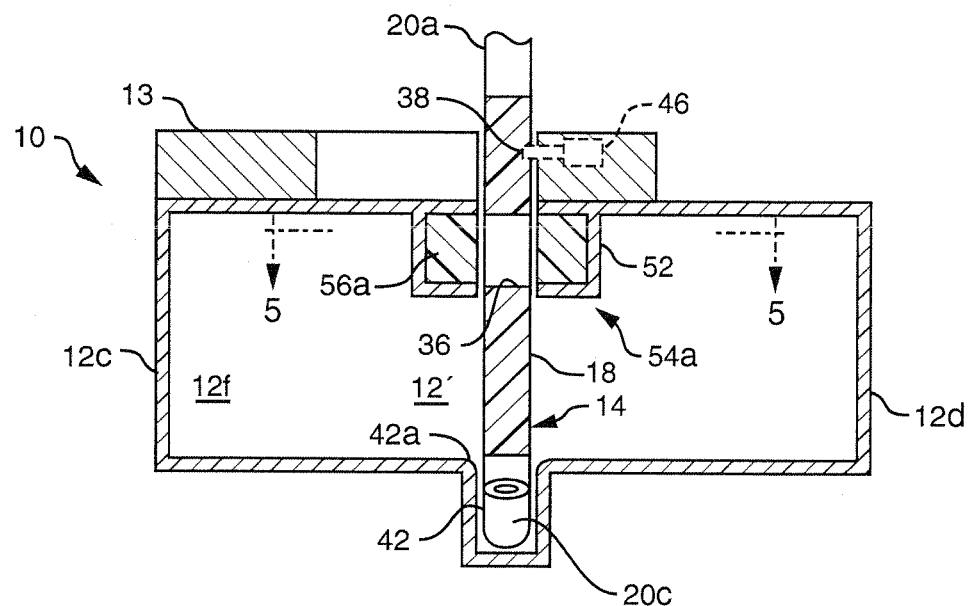
FIG. 4 is a sectional view taken along line 4-4 of FIG. 1.
Figure 6:
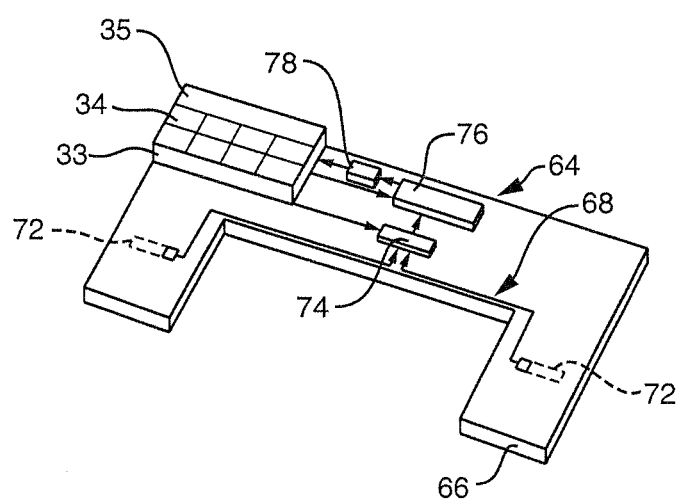
FIG. 6 is a diagrammatic view showing a portion of the FIG. 1 apparatus in greater detail.

Refer now to FIGS. 3 and 4, the bottom wall of 12b of waveguide 12 is formed with a narrow recess 42 which is positioned at the longitudinal axis (Z) of waveguide 12 directly opposite the slot 16 in housing 10. Recess 42 is shaped and arranged to snugly receive the segment 20c of the cartridge tube 20. Preferably, the outside corners 42a at the entrance to recess 42 are rounded or flared to help guide the lower end of cartridge 14 into recess 42 so that the cartridge will seat properly in the waveguide cavity 12'.

Recess 42 is dimensioned so that when the cartridge is seated, the axis A of tube segment 20c will be located at or just below the plane defined by edges 42a. This assures that the straight segments or legs 20a, 20b of that tube will be located in the heating cavity 12' of waveguide 12. On the other hand, at least part of the curved segment 20c of the tube in recess 42 is essentially embedded in the waveguide bottom wall 12b. Accordingly, that segment and its fluid contents have essentially no effect on the power attenuation characteristics of the apparatus.

Preferably, for maximum heating efficiency, the cartridge 14 is positioned in housing 10 so that the legs 20a and 20b are spaced from the adjacent waveguide end walls 12e and 12f, respectively, a distance equal to an integral multiple of a quarter wavelength at the heating frequency.

Thus, cartridge 14 may be inserted into the slot in housing 10 much like a credit card. When the cartridge is properly seated in the waveguide 12 as shown in FIG. 1, the spring-loaded plunger 46a of a microswitch 46 located in promontory 13 adjacent to slot 16 engages in the dimple 38 in the cartridge support member 18. This engagement serves not only to releasably retain the cartridge in housing 10, it also results in an enabling signal being sent to controller 33 so that the apparatus is operative only when the cartridge is properly seated in the housing.

Still referring to FIGS. 3 and 4, in accordance with the invention, waveguide 12 is formed with an internal conductive ridge or ridge guide 52 extending down from the waveguide top wall 12a at the longitudinal centerline of that wall. Ridge 52 has a generally rectangular cross-section being, for example, 0.45 inches high and twice as wide (inside dimension). It may extend the entire length of the waveguide 12 as shown or it may stop short of probe 32a. Also, while the illustrated ridge 52 is located entirely within the waveguide 12, it could extend up through waveguide wall 12a to some extent. If that is the case, slot 16 passes through the ridge into heating cavity 12'. Ridge 52 forms a high pass filter with a pass band of 3.75 to 4.2 GHz which is the temperature measuring or detection frequency band. In some applications, a band pass filter may be used to restrict the frequency band to that range. The fact that the illustrated ridge extends the full length of the waveguide 12 assures a broad-band impedance match at the heating frequency. As we shall see, segments of ridge 52 opposite the ends of slot 16 constitute a pair of receiving waveguides that form the above-mentioned transducers $T_I$ and $T_O$ which monitor the temperature of the fluid entering and leaving the cartridge 14 in the heating cavity 12'.

When the apparatus is in operation, microwave energy is emitted from probe 32a as shown in FIG. 3. As seen there, $P_0$ represents the applied power and the power attenuation is as follows:

$P_1 = P_0$ less the power absorbed by fluid in the tube leg 20b,
$P_2 = P_1$ less the power absorbed by fluid in the tube leg 20a,
$P_3$ = Power reflected at wall 12f constituting the waveguide back plate,
$P_3 = P_2$,
$P_4 = P_3$ less the power absorbed by fluid in the tube leg 20a,
$P_4 = P_3$ less the power absorbed by fluid in fluid leg 20b, and
$P_5$ = the remaining power not absorbed, or $P_4$ less the power absorbed by fluid in tube leg 20b.

As an example, an applied power of 100 watts and a single pass loss per fluid column in legs 20a, 20b of 3 dB would result in a total power absorbed of 93.7 watts. This is equivalent to 93.7% power absorbed and a return loss of approximately of 12 dB. Thus, the power absorbed by the fluid in tube 20 at heating cavity 12' is sufficient to heat that fluid to a desired temperature as the fluid flows through cartridge 14. The heating pattern produced by the waveguide 12 is evenly distributed between the tube inlet and outlet legs 20a and 20b. Half the power is absorbed in the initial pass and the remaining power which is reflected from waveguide wall 12f is absorbed by the fluid on the return pass so that the heating efficiency of the apparatus is quite high.

As shown in FIGS. 3 and 4, housing 10 contains at least one, and preferably two, receiving waveguides. To facilitate this, segments of the conductive ridge 52 opposite the ends of slot 16 are hollowed out to help form a pair of mirror-image receiving waveguides 54a and 54b. Preferably, the waveguides 54a and 54b are filled with a dielectric material 55 (e.g. K=4.5) so that the two waveguides can be relatively small yet provide a proper impedance match at the desired detection center frequency of 4.0 GHz. Each such waveguide 54a, 54b has one leg 56a which extends along the ridge and a second leg 56b which extends perpendicular to the ridge into the promontory 13. The two legs meet at a meeting wall 56c spaced a selected distance from the adjacent end of slot 16. Due to the presence of slot 16, each waveguide leg 56a is bifurcated at the slot, i.e. it includes two halves located on opposite sides of slot 16. While the two waveguides 54a, 54b are shown as being situated entirely within ridge 52, in some applications part or all of them may be located in promontory 13.

As best seen in FIGS. 3-5, when cartridge 14 is properly seated in housing 10, the two metallized notches 36 in support member 18 are located directly opposite the inner ends of the corresponding waveguide legs 56a so that the conductive upper and lower walls of each notch are essentially continuations or extensions of the upper and lower walls of the corresponding waveguide leg 56a, 56a, with the innermost wall of the notch helping to form the back plate for that leg, i.e. it fills in the space between the conductive inner ends of the waveguide leg 56a halves that are on opposite sides of slot 16 and completes the waveguide back plate.

On the other hand, the meeting wall 56c of each waveguide 54a, 54b is orientated at a 45° angle with respect to the ridge axis so that it constitutes an E-plane bend which redirects thermal radiation emanating from the adjacent leg of tube 20 and propagating along waveguide leg 56a vertically upwards into the corresponding waveguide leg 56b. In sum, the cartridge 14 structure and the ridge 52 structure combine and coact to provide the waveguides 54a and 54b that form the temperature sensing transducers $T_I$ and $T_O$, respectively, and lead the transducers outside heating cavity 12'. This mode of coupling to the outside is less lossy, less expensive and more forgiving than other coupling methods using coaxial connectors or probes, for example.

As best seen in FIGS. 3 and 5, each waveguide leg 56b leads to a waveguide-to-microstrip transition. Thus, for waveguide 54a there is a transition shown generally at 62a and for waveguide 54b there is a transition indicated generally at 62b. Preferably, the two transitions are mirror-images of one another and are part of a printed circuit board 64 that is mounted in housing 10, e.g. in promontory 13.

Circuit board 64 includes a substrate 66 and a printed circuit 68. Portions of substrate 66 extend into the waveguide legs 56b of each waveguide 54a, 54b. The substrate underside of each of those portions carries a microstrip 72 which projects into the associated waveguide leg 56b, being separated from the waveguide top wall 12a wall by an air gap 71 (FIG. 3) to form the transition 62a or 62b. These microstrips 72 are connected via plated through holes in substrate 66 to the remainder of the printed circuit 68 present on the upper surface of substrate 66 where the waveguide-generated outputs of the two transitions 62a and 62b are coupled by way of a switch 74 (SPST) to a radiometer 76 which may operate at a center frequency of 4.0 GHz. Both the switch and radiometer are controlled by the controller 33 which may be mounted on and connected to the printed circuit board 64. The switch and the radiometer preferably compromise a microwave integrated circuit (MIC) package which may be located directly above waveguide 12 close to the sensing transducers $T_I$ and as $T_O$, so as to minimize noise in the measured signal and to avoid the need for external cabling.

While the illustrated transitions 62a and 62b are microstrip transitions, other conventional transitions are possible such as a waveguide-to-stripline transition or a waveguide-to-coax-to-stripline transition.

When cartridge 14 is seated in housing 10 with fluid flowing through tube 20, that fluid will be warmed as it passes through the heating cavity 12' until the fluid reaches the temperature set by keypad 34. Since each sensing transducer $T_I$ or $T_O$ views only one leg of tube 20 and provides a direct measurement of the temperature of the fluid in that leg, it is important that the cartridge 14 be oriented in housing 10 so that the outlet or exit leg 20b of tube 20 terminated by the male connector 22b (FIG. 1) is the leg closer to the power source as shown in FIG. 3. To ensure this, the cartridge support member 18 may be provided with a polarity determination device, e.g. a longitudinal keyway 92 at one face thereof which is adapted to slidably receive a key 94 formed in the front edge of slot 16 as shown in FIG. 1. Then, when the cartridge bottoms in recess 42, the microswitch 46 will send an enabling signal to controller 33 indicating that the cartridge is properly seated in housing 10.

The apparatus may be turned on and off and be controlled via key pad 34 with the inlet and outlet temperatures being displayed in real time by display 35. The display may also display other parameters such as set point temperature, elapsed time, time of day, various diagnostics, etc.

The general operation of microwave warmers such as this is disclosed in my above patents.

When the apparatus 10 is in operation, the fluid flowing through the tube legs 20a and 20b in heating cavity 12' absorbs power and is heated as described above. The fluid in the tube segment 20c which is effectively outside the heating cavity is unaffected. The heat radiating from the fluid in the inlet leg 20a is sensed by transducer $T_I$ just as the fluid enters cavity 12' and a corresponding waveguide-generated signal is developed and applied via transition 62a and printed circuit 68 to switch 74. Similarly, thermal radiation heat from the fluid in the outlet leg 20b of tube 20 just as the fluid exits cavity 12' is sensed by transducer $T_O$ and a corresponding signal is applied via transition 62b to switch 74. Switch 74 may be toggled or switched by control signals from controller 33 to apply those waveguide-generated signals alternately to radiometer 76. As a result of this time sharing, the apparatus 10 requires only the one radiometer 76 that may be located inside the apparatus 10 right next to the transducers. The radiometer thereupon produces output signals accurately reflecting the fluid inlet and outlet temperatures. These signals may be applied by way of a conventional signal conditioning circuit 78 (filter, amplifier, A/D converter) to display 35 and also be used to control the transmitter as described in the above patents.

Since the transducers $T_I$ and $T_O$ sense the fluid right at the points where the fluid enters and leaves heating cavity 12', my apparatus also provides a very precise measurement of the flow rate through tube 20. More particularly, flow rate is determined by the following expression:

$$\frac{P(\text{watts})}{.07\Delta T(^\circ \text{ C.})} = \text{Flow Rate (ml/min.)}$$

where P=power absorbed (~equal to the applied power $P_0$), and $\Delta T$=the difference between the fluid inlet and outlet temperatures.

Of course, this flow rate can also be displayed by display 35. This is an important feature because a nurse cannot measure flow rates greater than about 25 ml/min. by counting drips in the drip chamber of a fluid administration set because at that rate, the drips become a steady stream. The present apparatus can measure and display even such high flow rates using the above calculation.

It is important to note that when my apparatus is in operation, little or no radiation may leak from the heating cavity 12' through slot 16 at both the heating and detection frequencies. This is because, as noted above, the slot 16 is quite thin or narrow and the slot is effectively extended in length upward through the promontory 13. Also, the metallized side wall segments of support member 18 adjacent the tube legs extend a selected distance above heating cavity 12' as to create with the conductive walls of promontory 13 adjacent to those legs a length of dielectric-filled circular waveguide that is cut-off at both the heating and detection frequencies, thereby further isolating heating cavity 12'. As radiation leakage from slot 16 is minimized, so also is the coupling of external radiated interference into the apparatus 10 via slot 16 which could adversely affect the measured temperature. In other words, the promontory 13 and cartridge 14 structures at the mouth of slot 16 and the narrow slot itself combine and coact to create waveguide "chimneys" above heating cavity 12' which function as two-way filters to prevent radiation from entering or leaving the cavity. In addition, the promontory itself wraps around the cartridge to provide a guide for, and stabilizing influence on, the cartridge.

Figure 7:
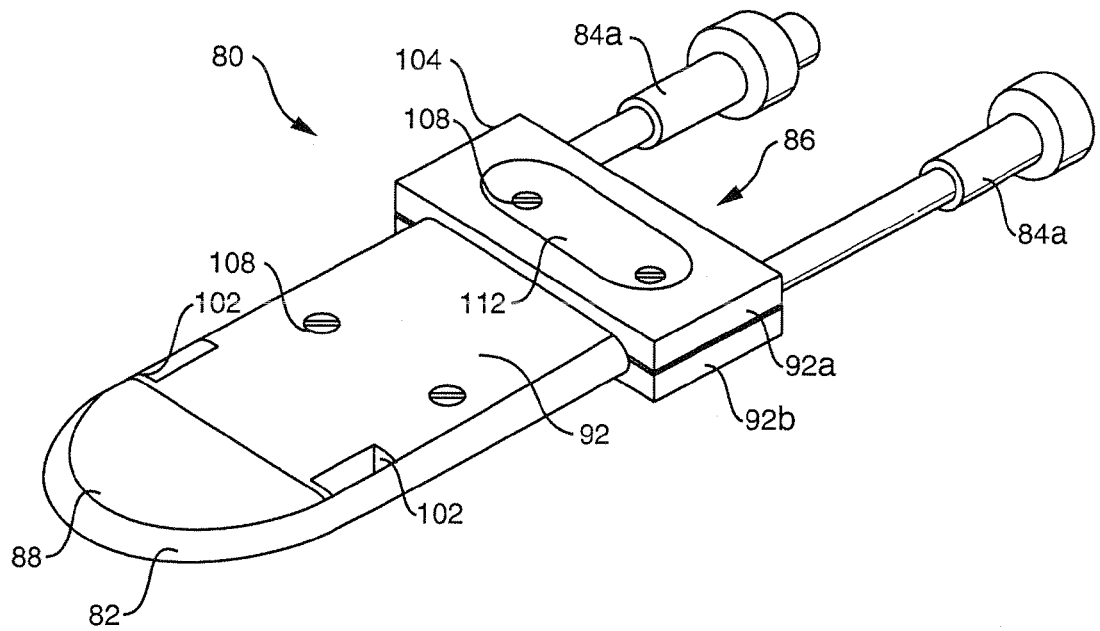
FIG. 7 is an isometric view of a second cartridge embodiment for use in the FIG. 1 apparatus.
Figure 7A:
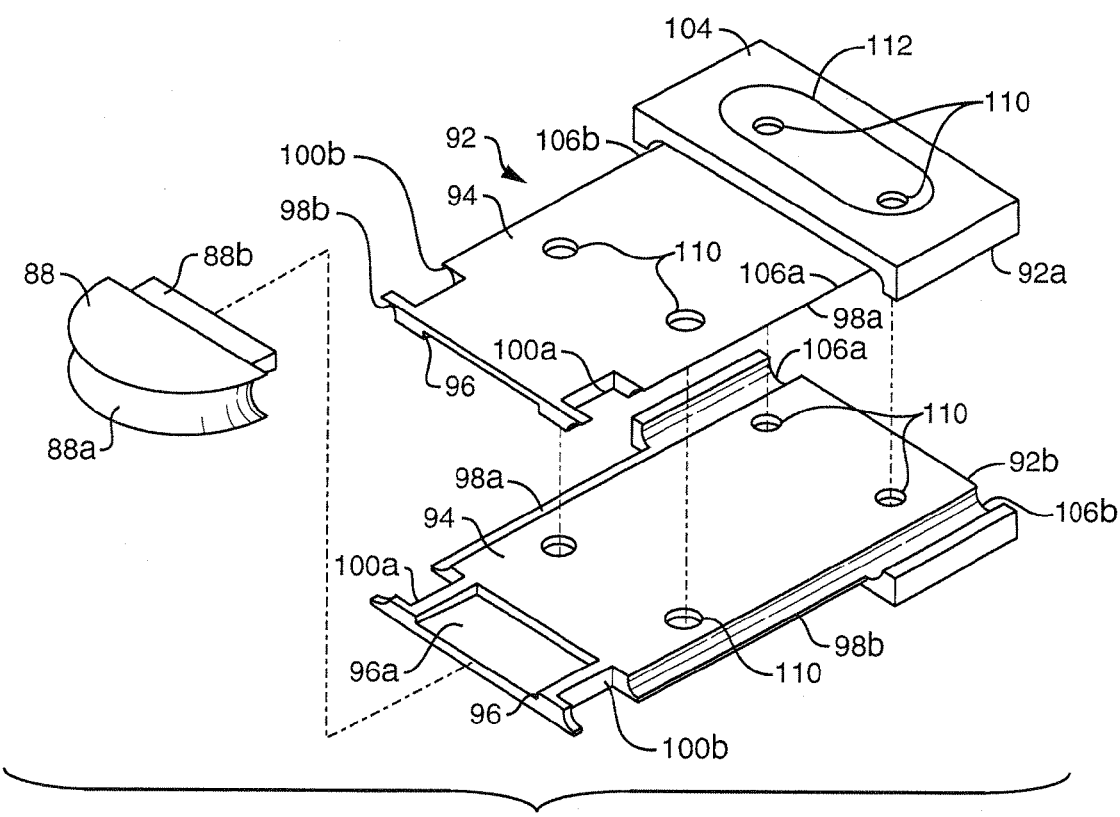
FIG. 7A is an exploded perspective view showing a part of the FIG. 7 cartridge in greater detail.

Refer now to FIG. 7 illustrating another in-line cartridge embodiment 80 which is especially easy to manufacture. Like cartridge 14, it includes a single loop of plastic tubing 82 having end connectors 84a and 84b. In this case, the U-shape of the loop is maintained by a support member shown generally at 86 composed of a plurality of separate parts or sections. As best seen in FIG. 7A, support member 86 comprises a lower end section 88 having a curved edge 88a with a concave cross-section enabling the curved end segment of tubing 82 to be recessed into that edge. Projecting from the opposite straight edge of section 88 is a tenon 88b. Support member 88 is made entirely of a dielectric material and may be molded of plastic using simple die parts.

The support member 86 also includes an upper section 92 that is made entirely of metal. To facilitate its manufacture, section 92 is composed of two substantially identical half sections 92a and 92b which are disposed in mirror-image, face-to-face contact so as to capture the opposite legs of the tube loop as shown in FIG. 7.

As shown in FIG. 7A, each half section 92a, 92b includes a generally rectangular plate 94 having a relatively wide groove 96 extending in from one end. The wide face 96a of that groove is sloped so that when plates 94, 94 of the two half sections 92a, 92b are brought together in face-to-face contact, the two grooves 96, 96 combine to form a mortise that captures the tenon 88b of the end section 88. Thus, the support member 86 has a dovetail connection between its plastic end section 88 and metal upper section 92. An equivalent embodiment may have a tenon projecting from section 92 into a slot in section 88.

Each plate 94 also has opposite side edges 98a and 98b with arcuate cross-sections so that when the plates of the two half sections 92a and 92b are brought together, those side edges form troughs to recess the legs of the tube loop as shown in FIG. 7.

Also extending in from the side edges 98a, 98b of each plate is a pair of mirror-image cutouts 100a and 100b. When the half sections 92a and 92b are assembled as shown in FIG. 7, these cutouts together define two mirror-image notches 102, 102 at the opposite sides of the support member which are bridged by the tubing 82. As discussed above, these notches complete the receiving waveguides in housing 10.

Each plate 94 has an end segment 104 remote from its channel 96 which is wider and thicker than the remainder of the plate. The opposite sides of that wider segment 104 accommodate a pair of semi-cylindrical grooves 106a and 106b. These grooves 106a, 106b are collinear to the corresponding arcuate side edges 98a, 98b of each plate so that when the two half sections 92a and 92b are brought together as shown in FIG. 7, the opposite legs of the tubing 82 are captured by the end segments 104, 104 of the two plates.

The two half sections 92a, 92b of support member section 92 may be secured together by fasteners 108 extending through aligned holes 110 in the two half sections 92a, 92b.

A big advantage of the cartridge 80 in FIG. 7 is that the components of its support member 86 can be molded without requiring compound dies.

The thicker upper end of the support member 86 formed by segments 104, 104 provides an insertion stop when the cartridge is slid into the slot 16 of the housing 12 in FIG. 1. It may also function as a handle for gripping cartridge 80. To facilitate such gripping, finger-receiving recesses 112 may be formed in the outer faces of segments 104, 104.

When cartridge 80 is inserted into housing 12 (FIGS. 1 and 3), the metal-wall notches 102, 102 form part of the transducers $T_I$ and $T_O$ and the nonconductive end section 88 of the support member is positioned in the heating cavity 12' of the housing as described above. The thicker segments 104, 104 of the support member 86 also form a flange at the entrance to the cartridge insertion slot 16 (FIG. 1) that short circuits the slot, further inhibiting radiation leakage therefrom and/or degraded temperature measurements due to interference from external electrical sources.

Figure 8:
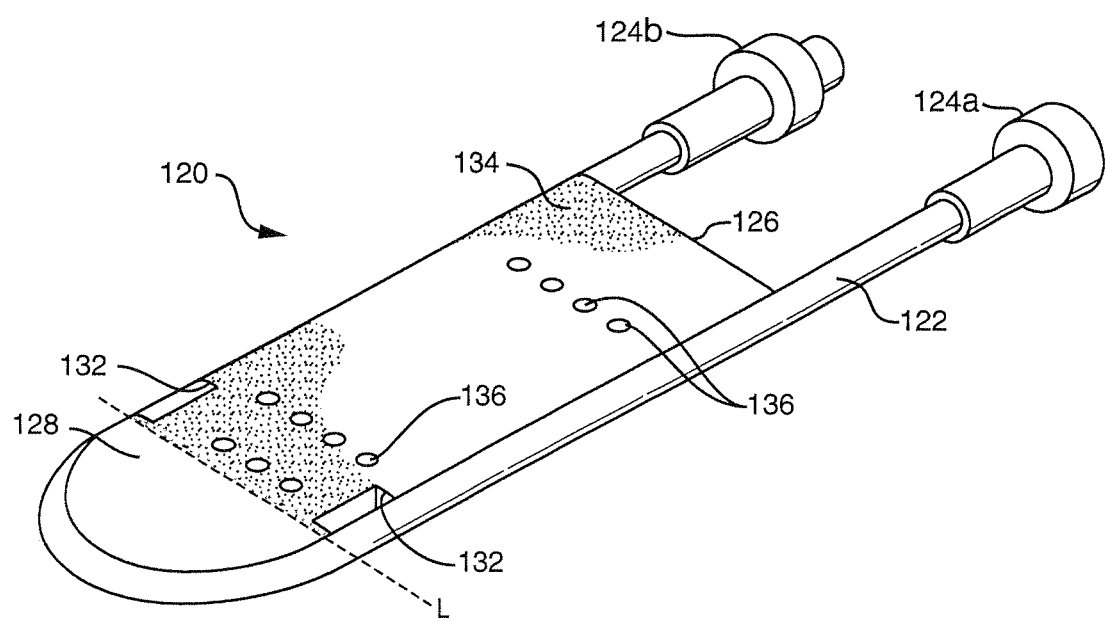
FIG. 8 is a view similar to FIG. 7 of a third cartridge embodiment.

FIG. 8 illustrates yet another in-line cartridge embodiment 120 which includes the usual single loop of tubing 122 having end connectors 124a and 124b. The shape of the tubing loop is maintained by a support member 126 comprising a rigid, molded plastic dielectric plate 128. Preferably, plate 128 has edges with concave cross-sections into which tubing 122 may be recessed. Also as with the other cartridges, mirror-image notches 132, 132 are present at the opposite sides of plate 128 which are bridged by the tubing.

As shown in FIG. 8, the surfaces of support member plate 128 above a line L extending across the plate just below notches 132, 132 are covered by an electrically conductive coating 134, e.g. by metallizing or painting that segment of the plate. Preferably also, through-holes 136 are provided in plate 128 above line L whose surfaces also carry the conductive coating 134 to electrically connect the opposite sides of the support member.

The non-conductive segment of the support member 126 below line L is the portion inserted into the heating cavity 12' of housing 12 in FIG. 3. As with the other cartridge embodiments, the conductive segment of the support member 126 above line L prevents radiation leakage through the cartridge insertion slot 16 (FIG. 1) and the notches 132, 132 complete the receiving waveguides 54a, 54b of the transducers $T_I$ and $T_O$, respectively, as in FIG. 3.

To simplify molding the support member 126, it may be formed as two identical half sections secured together in mirror-image face-to-face contact in the manner of the half sections 92a, 92b in FIG. 7. For this purpose, countersunk holes may be formed in the two half sections to receive fasteners that secure together to the two half sections. Alternatively, the two half sections may be held together by mating pegs and holes projecting from the opposing faces of the two half sections. Also, the support member 126 may be formed with an enlargement at its upper end similar to the one in FIG. 7.

In some applications, the warming apparatus may utilize a cartridge with tubing having an unusually large diameter. When such a cartridge is seated in the apparatus, the segments of the tubing bridging the notches in the support member constitute relatively large loads at the inner ends of the receiving waveguides 54a and 54b (FIG. 3). Therefore, in that event, it may not be necessary for the notch walls to be electrically conductive because the waveguides should function adequately without back plates.

In the various cartridge embodiments, 14, 80, 120, a pair of mirror-image, rectangular notches are present in their support members. It is possible that in some applications, a cartridge may be inserted into housing 10 at an angle to the longitudinal axis of the waveguide 52. In that event, in order to complete the receiving waveguides 54a, 54b, the notches in the cartridge support member may be triangular or have some other shape.

Also, if a particular application requires that only a single temperature measurement of the tube contents be taken, i.e. either the inlet or outlet temperature, one of the receiving waveguides 54a, 54b may be omitted, thereby obviating the need for two notches in the associated cartridge.

It will thus be seen that the objects set forth above, among those made apparent from the preceding description, are efficiently attained. Also, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. A microwave warming cartridge comprising a plate-like support member having upper and lower ends and spaced-apart parallel side edges extending between said ends, said ends and side edges forming a support member perimeter; a notch in one of the side edges of the support member, said notch having a bottom wall; a second notch in the other of the side edges of the support member both said notches having walls which are electrically conductive; a single tube loop extending along the perimeter of the support member, said tube loop having an inlet, an outlet and legs connected by a connecting segment, and securements securing the loop to the support member so that the loop legs engage said side edges and a segment of each leg bridges the adjacent notch opposite the bottom wall thereof.

2. The cartridge defined in claim 1 wherein the support member has front and rear upper surfaces adjacent to said upper end that are electrically conductive.

3. The cartridge defined in claim 2 wherein the support member is a dielectric part with a metal coating at said notch walls and said upper surfaces.

4. The cartridge defined in claim 1 wherein the tube loop is U-shaped with parallel coplanar legs.

5. The cartridge defined in claim 1 wherein the support member has the same shape as the tube loop.

6. The cartridge defined in claim 1 and further including a switch actuator on said support member.

7. The cartridge defined in claim 1
wherein said inlet comprises a female connector and said outlet comprises a male connector, and
further including a polarity determinator on the support member.

8. The cartridge defined in claim 1 wherein, said legs of the tube loop extend within said side edges of the support member.

9. The cartridge defined in claim 1 wherein
the support member includes a first section which extends from said upper end to a boundary line that lies just below said notches and a second section which extends from said boundary line to said lower end, and
the surfaces of the first section are electrically conductive and the surfaces of the second segment are electrically non-conductive.

10. The cartridge defined in claim 9 wherein the support member is of a dielectric material and said upper surfaces of the support member above said boundary line have a metal coating.

11. The cartridge defined in claim 9 wherein
said lower end and side edges of the support member are contiguous to the tube loop;
the support member is composed of two similar half sections, each half section extending above and below said boundary line and being positioned in mirror-image, face-to-face contact with the other half section, and
securements for securing together the two half sections.

12. The cartridge defined in claim 11 wherein the opposite side edges and said lower end of the support member define grooves that receive the tube loop.

13. The cartridge defined in claim 11 and further including one or more electrical connections between said half sections, said connections being located in the first section of the support member.

14. The cartridge defined in claim 9 wherein
the first section of the support member is of metal, and
the second section of the support member is a separate electrically non-conductive part.

15. The cartridge defined in claim 14 wherein
the opposite side edges of the support member are recessed to receive said tube loop, and
said first section is composed of two similar half sections positioned in mirror-image, face-to-face contact, fasteners for securing together said half sections, and a securing device for securing the second section to the first section at said boundary line.

16. The cartridge defined in claim 15 wherein the securing device comprises a tenon projecting from one of said second section and said first section into a mortise defined in the other of said second section and said first section by the opposing faces of said two half sections.

17. The cartridge defined in claim 1 wherein said support member has an upper end margin which encircles the legs of the tube loop.

18. The cartridge defined in claim 17 wherein said legs of the tube loop extend through said upper end margin.

19. A microwave warming cartridge comprising
a plate-like support member having upper and lower ends and opposite side edges forming a support member perimeter;
a pair of notches in said opposite side edges at a selected spacing from said lower end, said notches having electrically conductive walls, and
a tube extending along the support member perimeter and being engaged to said opposite side edges, said tube having a connecting segment extending under said lower end, an inlet and an outlet located above said upper end, and a pair of bridging segments bridging said pair of notches opposite the corresponding notch bottom walls and connecting the connecting segment to the inlet and outlet.

20. The cartridge defined in claim 19 wherein said notches are rectangular in shape.

21. The cartridge defined in claim 19 wherein the support member has surfaces adjacent to said upper end which are electrically conductive.

22. A cartridge assembly comprising
a microwave warming cartridge comprising
   a plate-like support member having upper and lower ends and spaced-apart parallel side edges extending between said ends, said ends and side edges forming a support member perimeter;
   a notch in one of the side edges of the support member, said notch having a bottom wall;
   a single tube loop extending along the perimeter of the support member, said tube loop having an inlet, an outlet and legs connected by a connecting segment:
   securements securing the loop to the support member so that the loop legs engage said side edges and a segment of one leg bridges the notch opposite the bottom wall thereof, and
heating apparatus having a heating cavity for seating said cartridge and heating any contents of said tube, said apparatus including a receiving waveguide positioned directly opposite said notch when the cartridge is seated in the heating cavity so that said notch forms an end wall of the receiving waveguide, said notch having an electrically conductive wall which constitutes a backplate for the receiving waveguide.

23. A cartridge assembly comprising the cartridge according to claim 19 and heating apparatus having a heating cavity for seating the cartridge and heating any contents of said tube, said apparatus including a pair of receiving waveguides positioned directly opposite said pair of notches when the cartridge is seated in the heating cavity so that each notch forms an end wall of the associated receiving waveguide.

24. The assembly defined in claim 23 wherein said electrically conductive walls of each notch include a bottom wall which constitutes a backplate for the associated receiving waveguide.

25. A cartridge assembly comprising
a microwave warming cartridge including
   a plate-like support member having upper and lower ends and spaced-apart parallel side edges extending between said ends, said ends and side edges forming a support member perimeter;
   a notch in one of the side edges of the support member, said notch having a bottom wall;
   a single tube loop extending along the perimeter of the support member, said tube loop having an inlet, an outlet and legs connected by a connecting segment;
   securements securing the loop to the support member so that the loop legs engage said side edges and a segment of one leg bridges the notch opposite the bottom wall thereof, and
heating apparatus having a heating cavity for seating the cartridge and heating any contents of said tube, said apparatus including a receiving waveguide positioned directly opposite said notch when the cartridge is seated in the heating cavity so that said notch forms an end wall of the receiving waveguide, said notch having an electrically conductive wall which constitutes a back plate for said waveguide.

26. The cartridge defined in claim 1 wherein said side edges of the support member encircle the tube legs at least part way along the lengths of said legs.

27. A cartridge for use in microwave warming apparatus and including a length of tubing having an inlet and an outlet, and a rigid support member having a perimeter and supporting the tubing wherein the tubing is composed of single loop extending along said perimeter and having at least one straight loop segment, and at least one notch is present in the support member perimeter which notch has a mouth bridged by said at least one loop segment and an electrically conductive bottom wall opposite said segment adapted to form the back end of a first receiving waveguide.

28. The cartridge defined in claim 27 including a second, similar notch in the support member whose mouth is bridged by a second similar loop segment and whose electrically conductive bottom wall is adapted to form the back end of a second receiving waveguide.

29. The cartridge defined in claim 28 wherein
   the support member is a plate-like structure having straight parallel opposite sides;
   said notches are formed in the opposite sides of that structure, and
   the tube loop is generally U-shaped and has a pair of straight, parallel legs extending along the opposite sides of the plate-like structure so that the segments thereof bridge of said notches.

30. Microwave warming apparatus comprising
   a housing having walls including a pair of longitudinal walls, forming a heating waveguide that defines a heating cavity;
   a slot extending through one longitudinal wall into the heating cavity, the slot adapted to receive a cartridge including a tube so that the tube extends through the slot into the heating cavity;
   a device to heat the contents of the tube, and
   a receiving waveguide for picking up thermal radiation emanating from the tube and producing a corresponding waveguide-generated signal indicative of the temperature of the fluid, wherein the receiving waveguide is composed of a waveguide portion which extends along said one longitudinal wall and opens into the slot, said receiving waveguide portion adapted to be completed by a cooperating receiving waveguide supplement contained in the cartridge when the cartridge is received in the slot, said supplement including a notch having an electrically conductive bottom wall opposite the tube, said wall constituting a back plate of said receiving waveguide.

* * * * *

UNITED STATES PATENT AND TRADEMARK OFFICE
CERTIFICATE OF CORRECTION

PATENT NO.        : 8,440,949 B2  
APPLICATION NO.   : 12/115075  
DATED             : May 14, 2013  
INVENTOR(S)       : Kenneth L. Carr It is certified that error appears in the above-identified patent and that said Letters Patent is hereby corrected as shown below:

In the Specification

In col. 14, line 12 should read:  
ing the tubing wherein the tubing is composed of a single loop Signed and Sealed this  
Twenty-fifth Day of June, 2013

Teresa Stanek Rea  
*Acting Director of the United States Patent and Trademark Office*